(12) United States Patent
Rogers et al.

(10) Patent No.: US 8,399,019 B2
(45) Date of Patent: Mar. 19, 2013

(54) ORAL DELIVERY VEHICLE AND MATERIAL

(75) Inventors: Ed Rogers, Alabaster, AL (US); Roy W. Gilbert, Alabaster, AL (US)

(73) Assignee: Foodsource Lures Corporation, Alabaster, AL (US)

( * ) Notice: Subject to any disclaimer, the term of this patent is extended or adjusted under 35 U.S.C. 154(b) by 0 days.

(21) Appl. No.: 13/457,604

(22) Filed: Apr. 27, 2012

(65) Prior Publication Data

US 2012/0207799 A1   Aug. 16, 2012

Related U.S. Application Data

(62) Division of application No. 11/909,848, filed as application No. PCT/US2006/011428 on Mar. 28, 2006.

(60) Provisional application No. 60/665,703, filed on Mar. 28, 2005.

(51) Int. Cl.
*A61K 9/00* (2006.01)

(52) U.S. Cl. ......... 424/484; 424/400; 424/485; 424/488

(58) Field of Classification Search .................. None
See application file for complete search history.

(56) References Cited

U.S. PATENT DOCUMENTS

| | | |
|---|---|---|
| 2,827,376 A | 3/1958 | Breuer |
| 2,938,294 A | 5/1960 | Bachmann |
| 3,607,294 A | 9/1971 | Ernstrom |
| 3,876,603 A | 4/1975 | Makhlouf |
| 4,076,846 A | 2/1978 | Nakatsuka et al. |
| 4,245,420 A | 1/1981 | Carr |
| 4,362,748 A | 12/1982 | Cox |
| 4,375,481 A | 3/1983 | Kuwabara et al. |
| 4,463,018 A | 7/1984 | Carr |
| 4,664,857 A | 5/1987 | Nambu |
| 5,089,277 A | 2/1992 | Prochnow |
| 5,197,219 A | 3/1993 | Cook, Jr. et al. |
| 5,266,323 A | 11/1993 | Guthrie et al. |
| 5,817,381 A | 10/1998 | Chen et al. |
| 6,001,382 A | 12/1999 | Levy |

(Continued)

FOREIGN PATENT DOCUMENTS

| | | |
|---|---|---|
| DE | 3333249 A1 | 3/1984 |
| DE | 4428763 A1 | 5/1996 |
| GB | 1465276 | 2/1977 |
| JP | 6319414 A | 11/1994 |
| JP | 2000060363 A | 2/2000 |
| WO | 02063952 A1 | 8/2002 |

OTHER PUBLICATIONS

"Berkley Power Naturals"; Berkley Fishing What's New; Jul. 29, 2002; 2 pgs.

(Continued)

*Primary Examiner* — Nissa Westerberg
(74) *Attorney, Agent, or Firm* — Gardner Groff Greenwald & Villanueva, PC

(57) ABSTRACT

Compositions for an oral delivery vehicle are described as well as methods for their manufacture and administration. The oral delivery vehicles can be made in any size or shape and can further comprise a medicament or other substance or object to be orally delivered. The vehicle can, for example, take the form of a pouch or capsule. Alternatively, a medicament or other substance to be orally delivered can be coated with the composition. In another alternative, the medicament or other substance to be orally delivered can be dispersed within a matrix of the composition. The compositions for the oral delivery vehicle are also suitable for use as an animal food or treat or use as a hunting bait or lure.

8 Claims, 1 Drawing Sheet

A

B

C

D

U.S. PATENT DOCUMENTS

| | | | | |
|---|---|---|---|---|
| 6,010,705 A | * | 1/2000 | Thune et al. | 424/234.1 |
| 6,037,039 A | | 3/2000 | Koike et al. | |
| 6,171,632 B1 | | 1/2001 | Lanter et al. | |
| 6,174,525 B1 | | 1/2001 | Kelley | |
| 6,176,632 B1 | | 1/2001 | Kageyama et al. | |
| 6,753,004 B2 | * | 6/2004 | Ollis et al. | 424/410 |
| 2003/0066231 A1 | * | 4/2003 | Ollis et al. | 43/42.24 |

OTHER PUBLICATIONS

International Search Report for PCT/US02/27862; Feb. 11, 2003; 2 pgs.

International Search Report for PCT/US06/11428; Sep. 21, 2006; 1 pg.

* cited by examiner

A 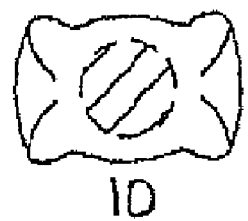
10
B 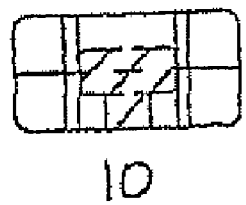
10
C 
10
D 

ORAL DELIVERY VEHICLE AND MATERIAL

CROSS-REFERENCE TO RELATED APPLICATION

This application is a divisional of U.S. Non-Provisional patent application Ser. No. 11/909,848 filed May 13, 2008, which is a U.S. National Phase of International PCT Patent Application Serial No. PCT/US2006/011428 filed Mar. 28, 2006, which claims the benefit of U.S. Provisional Patent Application Ser. No. 60/665,703 filed Mar. 28, 2005, which are hereby incorporated herein by reference in their entireties for all purposes.

FIELD OF THE INVENTION

The present invention relates generally to the field of materials and manufacturing, and more particularly to edible compositions and methods for the production of items including oral delivery vehicles for various substances, e.g., medicaments.

BACKGROUND

Various substances need to be orally delivered to animals, for example, medicine, vaccines, vitamins/minerals, and other substances. Often these substances are not good tasting or smelling or otherwise pose administration problems for delivery.

The provision of an effective edible oral delivery vehicle produced from natural and/or food grade ingredients would help alleviate these and other issues surrounding oral administration of various medicaments and other substances.

Thus, it can be seen that needs exist for improved edible materials and methods for producing oral delivery vehicles. It is to the provision of materials and methods meeting these and other needs that the present invention is primarily directed.

SUMMARY

Example embodiments of the present invention provide a low-cost, edible oral delivery vehicle composed of natural and/or food grade ingredients and a method for its production. Specifically, a delivery vehicle has been developed which can digest in the gastrointestinal tract of animals and make oral administration of various substances or objects easier and more palatable. Example embodiments of the present invention provide a delivery vehicle that withstands typical handling until it can be administered. Embodiments of the invention also successfully withstand typical storage conditions.

Medicines, vaccines, vitamins, minerals and/or other substances or objects can be added to a composition of the invention without significantly affecting the material's look and feel. Waste products from the manufacturing process of the composition can be easily recycled, composted, and/or even used as a food source for animals. Also, because the material of example embodiments of the invention is comprised of natural and/or food-grade ingredients, a wide array of biological organisms, such as insects and other animals, bacteria, fungi and the like, can consume and at least partially digest the material, thereby speeding the breakdown of discarded objects made of the material.

In one aspect, the invention includes an oral delivery vehicle comprising a shape formed of a flexible and resilient material. The flexible and resilient material preferably includes at least one carbohydrate and at least one protein. The material can be formed, for example, into the general shape of a natural food source of an animal or any other desired shape. The invention includes an oral delivery vehicle comprising a shape formed of a flexible and resilient material comprising about 30 to about 95 wt % on a solids basis of at least one natural or food grade carbohydrate, about 3 to about 50 wt % on a solids basis of at least one natural or food grade protein, and about 1 to about 10 wt % on a solids basis of at least one natural or food grade water-soluble gum, wherein the shape is suitable for oral administration to an animal. A vehicle of the invention can further comprise a medicament or other substance or object to be orally delivered.

In another aspect, the invention includes a material wherein the carbohydrate is preferably a monosaccharide, a disaccharide, a polysaccharide, a starch, or mixture thereof. The protein preferably is a gelatin, a casein, a whey, a gluten, a soy protein, an albumin, or mixture thereof. The water-soluble gum preferably is a xanthan gum, carrageenan, guar gum, locust bean gum, arabinogalactan, gum arabic, agar, pectin, or a mixture thereof.

In yet another aspect, the invention includes an edible oral delivery material wherein the material has an Instron 5 hardness of between about 1 kg to about 4 kg, and allows at least about 25% elongation before breakage.

One example embodiment of a delivery vehicle of the invention is a chewable "pouch." The pouch can be used with any type of medicament or other substance to be ingested. Another example embodiment of a delivery vehicle is a hollow capsule.

Another example embodiment of the invention is a coating for oral delivery. A medicament or other substance can be coated with the material and administered to an animal.

Yet another example embodiment of the invention is an admixture of a medicament or substance to be orally delivered and the material (using the material as a "matrix") formed into a desired shape.

The final form of the combination medicament/material can take on a variety of shapes and sizes.

Various embodiments can also be used in combination. For example, one medicament may be admixed into the material and the material formed into a pouch; then, a second medicament can be placed into the pouch.

The invention includes an oral delivery vehicle made by a process comprising mixing components comprising water, at least one natural or food grade carbohydrate, at least one natural or food grade protein, and at least one natural or food grade water-soluble gum to form a solution composition suitable for delivering a substance or object orally to an animal. The vehicle can be made by a process further comprising shaping the composition to form an oral delivery vehicle and/or further comprising curing the shaped composition to form an oral delivery vehicle.

In yet another aspect, the invention includes a process for producing an edible oral delivery material. The process preferably includes mixing components comprising at least one natural carbohydrate and at least one natural protein to form a composition; molding the composition into a desired shape; and curing the molded composition to produce a material that is flexible and resilient, and that allows at least about 25% elongation before breakage. The process can comprise mixing components comprising at least one natural carbohydrate and at least one natural protein to form a composition; coating the composition onto a substance to be delivered orally to an animal; and curing the composition-coated substance. A process can comprise mixing components comprising at least one natural carbohydrate and at least one natural protein to form a composition; shaping the composition into a desired shape; and curing the molded composition to produce a material. A method of the invention can further comprise adding a substance or object to be delivered to the cured material.

The invention includes a method for delivering a substance or object to an animal comprising providing an oral delivery vehicle comprising a shape formed of a flexible and resilient material, the material comprising about 30 to about 95 wt % on a solids basis of at least one natural or food grade carbohydrate; about 3 to about 50 wt % on a solids basis of at least one natural or food grade protein; and about 1 to about 10 wt % on a solids basis of at least one natural or food grade water-soluble gum, wherein the shape is suitable for oral administration to an animal, and further comprising a substance or an object to be delivered; and administering the oral delivery vehicle to an animal.

These and other aspects, features and advantages of the invention will be understood with reference to the drawing FIGURE and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING

The accompanying drawing, which is incorporated in and constitutes a part of this specification, illustrates several aspects described below. Like numbers represent the same elements throughout the FIGURE.

The drawing FIGURE shows a mold for molding a pouch constructed of a material according to an example embodiment of the present invention. View A=top view; B=side view; C=bottom view; and D=view of cavity core pin over the cavity opening.

DETAILED DESCRIPTION

The present invention may be understood more readily by reference to the following detailed description of the invention taken in connection with the accompanying drawing FIGURE, which form a part of this disclosure. It is to be understood that this invention is not limited to the specific devices, methods, conditions, or parameters described and/or shown herein, and that the terminology used herein is for the purpose of describing particular embodiments by way of example only and is net intended to be limiting of the claimed invention.

Also, as used in the specification including the appended claims, the singular forms "a," "an," and "the" include the plural, and reference to a particular numerical value includes at least that particular value, unless the context clearly dictates otherwise. Thus, for example, reference to "an attractant" includes mixtures of attractants; reference to "a medicament" includes mixtures of two or more such medicaments, and the like.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

"Optional" or "optionally" means that the subsequently described event or circumstance may or may not occur, and that the description includes instances where the event or circumstance occurs and instances where it does not. For example, the phrase "optionally adding additives" means that the additives may or may not be added and that the description includes both addition of additives and no addition of additives.

A weight percent of a component, unless specifically stated to the contrary, is based on the total weight of the formulation or composition in which the component is included.

As used herein, "natural" or "naturally occurring" includes materials occurring in nature, as well as man-made or synthesized materials identical to materials occurring in nature.

"Food grade" as used herein means considered safe for use in food by an agency regulating food such as the U.S. Food and Drug Administration or as determined by Food Chemicals Codex specifications.

In example embodiments, the present invention includes a material comprising naturally occurring or food grade carbohydrates and proteins. Various example embodiments of a material of the present invention are discussed in U.S. Pat. No. 6,753,004, U.S. 2004/0170662, U.S. 2004/0234570, and below in the Examples.

A material of the invention comprises a carbohydrate. A carbohydrate component of the material is preferably selected from natural or food grade carbohydrates such as a monosaccharide; disaccharide, polysaccharide, starch, or mixtures thereof. Specifically, for example, the carbohydrate can be glucose, fructose, sucrose, lactose, maltose, cellobiose, glycerol, corn starch, wheat starch, rice starch, potato starch, or mixtures thereof.

A material of the invention comprises a protein. A protein component of the material is preferably selected from natural or food grade protein including, for example, casein, whey protein, gelatin, gluten, soy protein, albumin, or mixtures thereof.

A material of the invention can comprise a water-soluble gum. A water-soluble gum component of the material is preferably selected from natural or food grade water-soluble gum including, for example, xanthan gum, carrageenan, guar gum, locust bean gum, arabinogalactan, gum arabic, agar, pectin, or mixtures thereof.

An example embodiment of a material of the invention comprises about 30 to about 95% carbohydrate, about 3 to about 50% protein, and about 1 to about 10% water-soluble gum, wherein the percentages are weight percentages on a solids basis. The material can comprise, for example, about 30, 32, 35, 37, 40, 43, 45, 46, 48, 50, 51, 54, 55, 59, 60, 62, 64, 65, 66, 68, 70, 71, 73, 75, 77, 79, 80, 83, 85, 87, 89, 90, 92, 94, or 95 wt % carbohydrate, on a solids basis. The material can comprise, for example, about 3, 5, 7, 9, 10, 12, 14, 15, 17, 20, 22, 25, 26, 28, 30, 33, 35, 37, 40, 41, 43, 45, 46, 48, or 50 wt % protein, on a solids basis. The material can comprise, for example, about 1, 1.2, 1.5, 1.7, 2, 2.3, 2.5, 2.8, 3, 3.1, 3.5, 3.6, 3.8, 4, 4.3, 4.5, 4.6, 4.9, 5, 5.2, 5.5, 5.7, 6, 6.2, 6.5, 6.8, 7, 7.1, 7.3, 7.5, 7.8, 7.9, 8, 8.4, 8.5, 8.7, 9, 9.1, 9.3, 9.5, 9.7, or 9.8 wt % water-soluble gum, on a solids basis.

In preferred form, a material of the present invention comprises at least one sugar, at least one carbohydrate polymer, and at least one protein; in which the weight percentage content of sugar, carbohydrate polymer, and protein components range from about 50% to about 90%, about 2% to about 15%, and about 15% to about 40%, respectively, on a solids basis. In a further preferred embodiment, a material of the present invention comprises natural sugar, natural carbohydrate polymer, and natural protein components in the ranges of about 50% to about 90%, about 5% to about 15%, and about 15% to about 30%, respectively, on a solids basis.

A material of the invention can further optionally comprise salts, food grade preservatives, flavoring agents, nutrients, vitamins, minerals, and/or other additives.

Attractants or feeding stimulants are also optionally included, such as natural diet enhancers (including, e.g., hydrolyzed fish proteins, fish oil, fish meat, ground crustaceans, ground mussels, fish powder, fruit, spices, garlic, garlic oil, extracts and the like); synthetic diet enhancers (including, e.g., mixtures of neutral L-amino acids, betaine, nucleotides (e.g., inosine, inosine-5-monophosphate), sulfonium compounds (e.g., dimethylthetin, dimethylpropiothetin) and the like); and/or visual attractants (including, e.g., metallized or metallic glitter, plastic and Mylar glitter, and/or food grade colors). Attractants or stimulants are optionally included in a material of the present invention in an amount of from about 2% to about 10%, or less, on a dry weight basis.

A material of the invention can comprise water. Water is generally used in preparing the material. Water can remain in the final material in varying amounts after processing (e.g., shaping and/or curing). In an example embodiment about 50 wt % to about 70 wt % of the water remains in a final material.

In particular example embodiments, a material of the present invention includes a blend of water, sucrose, gelatin, glycerol, kappa carrageenan, potassium chloride, a preservative, and a food coloring. In further preferred embodiments, the sucrose, gelatin, glycerol, kappa carrageenan, potassium chloride, and potassium sorbate ingredients are present in ranges of from about 30% to about 70%, about 3% to about 35%, about 20% to about 50%, about 2% to about 6%, about 0.1% to about 2.0%, and about 0.1% to about 2.0%, respectively, on a solids basis. In still further embodiments, the material further comprises an attractant/scent.

In other particular example embodiments, a material of the present invention includes a blend of water, sucrose, gelatin agar, calcium chloride, starch, corn syrup, glycerin and food coloring. In further embodiments, a material of the present invention includes a blend of sucrose, gelatin, sodium alginate, locust bean gum, calcium chloride, starch, corn syrup, glycerin, sodium benzoate and sodium metaphosphate, preferably present in ranges of from about 5% to about 15%, about 10% to about 30%, about 1% to about 5%, about 1% to about 5%, about 0.1% to about 1%, about 1% to about 5%, about 30% to about 50%, about 1% to about 5%, about 1% to about 3%, and about 1% to about 3%, respectively, on a solids basis. In still further example embodiments, the material further comprises an attractant/scent.

In still other particular example embodiments, a material of the present invention includes a blend of sucrose, gelatin, sodium alginate, calcium chloride, starch, sodium metaphosphate, corn syrup, glycerin, and food coloring. In still further particular example embodiments, the material further comprises an attractant/scent.

In an example embodiment, the invention includes a material comprising about 40 to about 50 wt % water, about 25 to about 40 wt % carbohydrate, about 0.1 to about 5 wt % gum, and about 5 to about 15 wt % protein. In particular an embodiment can comprise about 44 wt % water, about 26 wt % corn syrup, about 3 wt % glycerin, 11 wt % gelatin, about 8 wt % sucrose, about 2 wt % sodium alginate, about 1 wt % corn starch, about 1 wt % locust bean gum, about 1 wt % sodium metaphosphate, less than about 1 wt % calcium chloride, about 2 wt % scent/flavor, about 1 wt % food coloring, and about 1 wt % food preservative.

In an example embodiment, the invention includes a material made by a process comprising mixing about 30 to about 95% carbohydrate, about 3 to about 50% protein, about 1 to about 10% water-soluble gum, wherein the percentages are weight percentages on a solids basis, and water under conditions to form an essentially homogeneous solution composition. This process can further comprise shaping the composition. The shaping can be to a shape useful as an oral delivery vehicle. The process can further comprise curing the composition. An example embodiment is material made by a process comprising mixing about 30 to about 95% carbohydrate, about 3 to about 50% protein, about 1 to about 10% water-soluble gum, wherein the percentages are weight percentages on a solids basis, and water under conditions to form an essentially homogeneous solution composition; shaping the composition; and curing the shaped composition. In another embodiment of this material, the mixture, shaped composition, and/or cured composition can further comprise a substance or medicament to be delivered, e.g., drug, vaccine, vitamin/mineral, or mixture thereof.

A material of the invention includes a composition of the mixing step, a shaped composition, and/or also includes a cured composition of this process.

The invention can include an oral delivery vehicle comprising a material of the invention. An oral delivery vehicle of the invention can have many different physical embodiments, e.g., shapes and sizes. The shape of the vehicle can be regular or irregular. A final combination of a substance or object to be delivered and material can take on a variety of shapes and sizes. One of skill in the art can determine an appropriate size and shape depending on the end use desired, e.g., the targeted animal.

The material of the present invention can be used as a delivery vehicle for a variety of substances or objects. Examples include drugs (e.g., antibiotics or contraceptives), vaccines, biomarkers, vitamins, and minerals. Examples of objects include a tracking device or an instrument for transmitting vital signs.

A formulation of the material (examples of which are described herein throughout) can be one which masks or otherwise makes a substance/medicament, which can be bad tasting, more palatable to an animal.

In an example embodiment, and with reference to the drawing FIGURE, the present invention can comprise an oral delivery vehicle shaped by a mold 10 as a pouch made from one or more of the materials disclosed herein. The pouch can contain a substance to be orally delivered to a recipient of the pouch.

An embodiment of the invention is a coating for oral delivery. The coating can be for a substance or an object. For example, drugs, vaccines, or other delivered materials can be coated with a layer(s) of the natural edible material described herein. The coated substance or object can then be consumed by a target organism or delivered to an environment where the coating biodegrades or digests over time to expose and release the delivered substance or object. The administration of a coated substance or object of the invention is by conventional means. Conventional coating techniques can be used for coating a substance or object with the material of the invention, e.g., dipping.

A coating of the invention can be for time-release of a substance or object. By selectively controlling the thickness and/or content of the coating layer, for example, the delivery time can be controlled. For example, a quantity of a delivered, substance can be provided with coatings of varying duration, whereby different portions of the delivered substance are released at different times. The invention also includes the delivered substance or object coated with a natural edible material as described herein and a method of coating a delivered substance or object with the natural edible material.

Yet another example embodiment of the invention is to admix a medicament or substance or object to be orally delivered into the material (using the material as a "matrix") and then forming the admixture into a desired shape, for example, by molding.

Still other example embodiments of the invention include the use of one or more of the materials disclosed herein as a food or a treat for animals. Additives including vitamins, minerals, growth hormones, and the like are optionally included in a food material of the present invention.

Still other embodiments of the invention include an attractant or a food product for animals that is formed of a material comprising naturally occurring or food grade carbohydrates and proteins, as described herein. An embodiment of the invention is a bait or lure for an animal, e.g., a hunting bait or lure, comprising a material of the invention.

Other embodiments of the invention include methods for producing a material comprising naturally occurring or food grade carbohydrates and proteins and methods for producing oral delivery vehicles and other items and objects from such a material.

A substance or object to be orally delivered can be readily selected by one of ordinary skill in the art. For example, a medicine, vaccine, vitamin, mineral, or other drug, or combination thereof can be delivered by an oral delivery vehicle of the invention. A medicament or other substance(s) can be in any form, for example, liquid or solid (e.g., powder or pill). One of skill in the art can select the form for the medicament or other substance to be delivered (for ease of discussion, references to "medicament" throughout mean any substance desired to be delivered unless indicated to the contrary).

The amount/dosage of substance to be orally delivered (or number of objects) can be readily determined by one of ordinary skill in the art. As a general matter, an effective amount of the substance to be orally delivered is added to the delivery vehicle. An amount in addition to the effective amount may be necessary depending on whether all of the substance will be bioavailable once ingested or if a portion will be lost in the environment prior to ingestion. This additional amount can also be determined by one of ordinary skill in the art.

By the term "effective amount" of a substance as provided herein is meant a nontoxic but sufficient amount of the substance to provide the desired result. As is known, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation. The dosages or amounts of the substances described herein are large enough to produce the desired effect in the method by which delivery occurs. The dosage should not be so large as to cause adverse side effects, such as unwanted cross-reactions, anaphylactic reactions, and the like. The dosage can be adjusted based on the condition of the subject involved. The dose and/or schedule of doses can be varied.

Regardless of the physical embodiment, the material can be formulated and/or sized to provide a desired time-release profile to the substance/medicament or object. One of skill in the art can determine the formulation of material and amount of substance/medicament or object to use in order to produce a desired time-release profile.

An oral delivery vehicle of the invention can be used to deliver a substance or an object to any animal, for example, domestic animals and pets, wildlife, or even humans. For example, animals can include dogs, cats, fish, cattle, horses, raccoons, deer, and the like.

One embodiment of a delivery vehicle of the invention is a chewable pouch. See, e.g., FIGURE. The pouch can be used with any type of medicament or other substance to be ingested. For example, a medicine, vaccine, vitamin/mineral, or other drug, or combinations thereof can be inserted into a pouch. The medicament or other substances can be in any form, for example, liquid or solid (e.g., powder or pill).

Though the term "pouch" is used, the oral delivery vehicle can be in most any form. A pouch is a convenient form such that the pouches can be ready-made and the medicament or other substance simply placed in the pouch before delivery to the animal. One example structural embodiment of such a pouch is one which would be molded from the mold 10 illustrated in the FIGURE. In this description a "pouch" generally refers to any shape with a cavity therein which can be used to hold a medicament. Thus, for example, another embodiment is a hollow capsule.

Various embodiments of the invention can also be used in combination. For example, one medicament may be admixed into the material and the material formed into a pouch; then, a second medicament can be placed into the pouch.

Some properties of the material are, for example, it can hold a variety of scents, hold a variety of flavors, be edible, be digestible, contain nutritional value, be attractive to the recipient by smell, taste and texture, be easy to store, have a long shelf life, be durable, be biodegradable, and be capable of being formed into virtually any shape or size.

The present invention also includes a method for the manufacture of an oral delivery vehicle or other item from one or more of the materials disclosed herein. A method of making a material or oral delivery vehicle of the invention comprises mixing the ingredients/components together. Conventional mixing equipment and techniques can be used. Preferably, the mixing is for a length of time and/or in a manner sufficient to form an essentially homogeneous mixture.

A method of making a material or oral delivery vehicle of the invention can also comprise shaping the material or a medicament/material combination. The shaping can be by a variety of methods. For example, shaping can comprise molding the material before, during, or after addition of a medicament. The shaping can be by coating a substance or object with the material or a medicament/material combination. Shaping can be performed after curing as well. For example, the mixture can be poured into a pan, cured, and then cut into shapes.

A method of making a material or oral delivery vehicle of the invention can also comprise curing the material or a medicament/material or object combination. The curing can be by a variety of methods. For example, curing can comprise cooling the material and/or drying the material. The curing can be active or passive steps.

A method can further comprise adding a substance/medicament or object to the mixture, shaped material, and/or cured material.

In example embodiments, a method of the present invention preferably includes the mixing of components according to one or more of the formulas disclosed herein, the forming of the composition into various shapes (e.g., molding), and curing of the shape to develop its desired physical consistency and characteristics. In example embodiments, the process utilizes the same type of molds currently used to manufacture typical items.

The process can include placing a liquid material or material/medicament combination into an aluminum mold, cooling the mold to approximately 4-30° C. for less than 15 minutes, and releasing the formed shape or other item from the mold. Depending upon the formulation, curing at 4° C. for 20-44 hours ores high as 50° C. for 3-5 hours may be required. The rate of curing of the material has been found to be primarily a function of time, temperature, and relative humidity in a curing environment. Although the example embodiments described herein have been found to possess adequate curing characteristics at a wide range of typical ambient temperature and humidity, it may be desirable in some instances to provide a climate controlled manufacturing and curing facility to expedite production. Alternatively, the curing time can be adjusted depending on the existing ambient conditions.

The progress of the curing process can be monitored by measuring the weight loss of the material over time and/or by measuring the hardness and/or other characteristics of the material. Upon reaching a desired state of curing, the cured material can be spray-coated with a natural oil to prevent overdrying and maintain a desired feel and material consistency. Alternatively, the material can be packaged and sealed upon reaching the desired state of curing to prevent overdrying and maintain a desired feel and material consistency.

In example embodiments of the invention, cured shapes having acceptable feel, durability, and ingredients were tested using an Instron® testing apparatus with a load range of 5 and a speed of 200 mm/minute. A lizard-shape was gripped just below the neck and above the hind legs. The material was found to allow at least 25% elongation before breakage. Most preferably, the material allowed at least 100% elongation before breakage. Fracture preferably occurred after the force applied reached at least about 1 to about 1.5 kg. Compression testing of the material indicated a hardness of about 1 to about 4 kg. While materials having characteristics outside of these ranges can be achieved by increasing or decreasing the degree of curing, these characteristics have been shown to produce an article having a suitable combination of feel, durability, and ability to readily biodegrade and/or digest in the digestive tract of animals.

Items produced according to preferred and example embodiments of the present invention can quickly breakdown/degrade in the environment and digest in the stomachs of animals. Experiments conducted using example embodiments of the invention show typical biodegradation rates of less than 3 months in the environment, and swallowed items disappeared from animal (i.e., fish) gastrointestinal tracts within a week.

The present invention will be further understood with reference to the following examples:

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Formulation 1

A formulation of the following composition was prepared:

| Component | Amount |
| --- | --- |
| Water | 100 g |
| Sucrose | 30.3 g |
| Gelatin (200-300 bloom) | 3.0 g |
| Glycerol | 40.6 g |
| Kappa carrageenan | 2.0 g |
| Potassium chloride (KCl) | 0.44 g |
| Potassium sorbate | 0.48 g |
| Food coloring | trace |

Manufacturing Procedure: The mixing vessel was charged with the water, KCl, and gelatin at room temperature. After thorough agitating, the mixture was heated with continued stirring. The carrageenan was, added next, followed by the sucrose, glycerol, and food coloring. The sorbate was added last. Heating with agitation continued until the temperature reached around 90° C. At this point, all components were completely dissolved in solution and the mixture appeared homogeneous. The hot solution was injected using a syringe into a warm fish-shaped aluminum mold. The mold was then placed into an ice bath for about 10 minutes to get rapid gelation. The solidified items were removed from the molds. Freshly prepared items were brittle. Curing by either storing in the refrigerator for three days or heating at 50° C. for 4-5 hours gave a more flexible, tougher item. However, the resulting item shrank by about 50% as compared to the fresh item.

In water this shaped article felt slimy, begins to swell, and became more "wiggly." This formulation had a melting temperature greater than 60° C. When bass were force fed these shaped items, their stomach contents showed no signs of the item after a week.

Example 2

Formulation 2

A formulation of the following composition was prepared:

| Component | Amount |
| --- | --- |
| Water | 100 g |
| Sucrose | 20 g |
| Gelatin (200-300 bloom) | 4.0 g |
| Glycerol | 20 g |
| Kappa carrageenan | 2.75 g |
| Potassium chloride (KCl) | 0.66 g |
| Potassium sorbate | 0.5 g |
| Food coloring | trace |

Manufacturing Procedure: The mixing vessel was charged with the water, KCl, gelatin, and carrageenan at room temperature. After thorough agitating, the mixture was heated with continued stirring. Once the temperature reached 65° C., the sucrose, glycerol, sorbate, and food coloring were added. Heating with agitation continued until the temperature reached about 85° C. At this point, all components were completely dissolved in solution and the mixture appeared homogeneous. The hot solution was injected using a syringe into warm aluminum maids to yield fish-shaped and lizard-shaped objects. The molds were placed into an ice bath for about 10 minutes to rapidly obtain a firm gel. The solidified objects were removed from the molds.

Freshly prepared objects were brittle. Curing by either storing in the refrigerator for two days or heating at 50° C. for 4-5 hours gave a more flexible, tougher item. However, the item shrank by about 50%.

In water this shaped article felt slimy, began to swell, and became more "wiggly." This formulation had a melting temperature greater than 60° C.

Example 3

Formulation 3

A formulation of the following composition was prepared:

| Component | Amount |
| --- | --- |
| Water | 105 g |
| Sucrose | 50 g |
| Gelatin (200-300 bloom) | 10.0 g |
| Kappa carrageenan | 3.0 g |
| Potassium chloride (KCl) | 0.6 g |
| Potassium sorbate | 0.5 g |
| Powdered fish food | 1.0 g |
| Food coloring | trace |

Manufacturing Procedure: The mixing, vessel was charged with the water, KCl, and gelatin, which were stirred at room temperature. After thorough agitating, the mixture was heated with continued stirring. Once the temperature reached about 65° C., the sucrose, carrageenan, and food coloring were added. Heating with agitation continued until the temperature reached about 85° C., after which the sorbate and fish food, were added. When all components were completely dissolved in solution and the mixture appeared homogeneous, the hot solution was injected using a syringe into a warm aluminum molds to yield fish-shaped and lizard-shaped objects. The mold was placed into an ice bath for about 10 minutes to rapidly obtain, a firm gel. The solidified objects were removed from the molds. Freshly prepared objects were brittle. Curing by storing in the refrigerator for two days gave a more flexible, tougher object. Although the object shrank by about 50%, it swelled when hydrated.

Example 4

Formulation 4

A formulation of the following composition was prepared;

| Component | Amount |
| --- | --- |
| Water | 100 g |
| Sucrose | 50 g |
| Gelatin (200-300 bloom) | 15.6 g |
| Kappa carrageenan | 3.0 g |
| Potassium chloride (KCl) | 0.6 g |
| Potassium sorbate | 0.6 g |
| Powdered fish food | 2.0 g |
| Food coloring | trace |

Manufacturing Procedure: The water was brought to a boil while the other ingredients were dry blended. The mixing vessel was charged with the hot water. The dry ingredients were added to the hot water with lots of mixing. Food coloring was added. Heating with agitation continued until the temperature reached about 90° C. When all components were completely dissolved in solution and the mixture appeared homogeneous, the hot solution was injected using a syringe into warm aluminum molds to yield fish-shaped and lizard-shaped objects. The mold was placed into an ice bath for about 10 minutes to rapidly obtain a firm gel. The solidified objects were removed from the molds. Freshly prepared objects were brittle. Curing by storing in the refrigerator for 22 hours gave a more flexible, tougher object. This object shrank by about 20% in size and 30% in weight.

Thermal analysis by differential scanning calorimetry showed no melting peak below 100° C. (212° F.). An object stored for over two days at 60° C. (150° F.) maintained its shape. Instron® testing indicated the objects were of similar strength to similar-shaped rubber objects, but were less flexible.

The object became slimy when moistened, swelled when hydrated, and became more "wiggly" during hydration.

The biodegradability of this composition was evaluated by placing a fish-shaped object into a porous container, which was subsequently placed into a ten-gallon fish tank containing pond water. A filterless pump provided slight agitation to the water. This fish tank was designed to mimic a true aquatic environment. A second "disintegration" study was conducted by placing two lizard-shaped objects into the same apparatus. Monitoring the objects over time, it was seen that the objects were no longer detectable after 1 month.

Example 5

Formulation 5

A formulation of the following composition was prepared:

| Component | Amount |
| --- | --- |
| Water | 40 g |
| Sucrose | 10 g |
| Gelatin (200-300 bloom) | 14.2 g |
| Agar | 2.0 g |
| Calcium chloride (CaCl$_2$) | 0.5 g |
| Starch | 2.0 g |
| Corn Syrup | 25 g |
| Glycerin | 2 g |
| Food coloring | trace |

Manufacturing Procedure: All ingredients are weighed prior to processing. The water was brought to a boil while the other ingredients were dry blended. The mixing vessel was charged with the hot water. The dry ingredients were added to the hot water with lots of mixing. Food coloring was added. Heating with agitation continued until the temperature reached about 90° C. When all components were completely dissolved in solution and the mixture appeared homogeneous, the hot solution was injected using a syringe into an aluminum mold to yield fish-shaped and lizard-shaped articles. The mold was placed in a refrigerator for about 15 minutes to rapidly obtain a firm gel. The solidified articles were removed from the molds. Freshly prepared articles were brittle. Curing by storing at ambient temperature for 48 hours gave a tougher while still flexible article. This item shrank by about 10% in size and 20% in weight.

Analysis was conducted by holding the articles in a controlled environment for two hours at a temperature of 150° F. The article held at this temperature without melting. The article became slimy when moistened, swelled when hydrated, and became more "wiggly" during hydration. The tensile strength of the item was comparable of that of similar shaped plastic items when tested on the Instron® Universal Testing Instrument using manual grips.

Example 6

Formulation 6

A formulation of the following composition was prepared:

| Component | Amount |
| --- | --- |
| Water | 40 g |
| Sucrose | 10 g |
| Gelatin (200-300 bloom) | 14.2 g |
| Sodium Alginate | 3.0 g |
| Calcium chloride (CaCl$_2$) | 0.5 g |
| Starch | 2.0 g |
| Sodium Metaphosphate | 1.0 g |
| Corn Syrup | 25 g |
| Glycerin | 2 g |
| Food coloring | trace |

Manufacturing Procedure: All ingredients are weighed prior to processing. The water was brought to a boil while the other ingredients were dry blended. The mixing vessel was charged with the hot water. The dry ingredients were added to the hot water with lots of mixing. Food coloring was added. Heating with agitation continued until the temperature reached about 90° C. When all components were completely dissolved in solution and the mixture appeared homogeneous, the hot solution was injected using a syringe into an aluminum mold to yield fish-shaped and lizard-shaped articles. The mold was placed in a refrigerator for about 15 minutes to rapidly obtain a firm gel. The solidified articles were removed from the molds. Freshly prepared articles were brittle. Curing by storing at ambient temperature varies with humidity and may range from about 10-30 hours, and gives a tougher while still flexible article. This article shrank by about 10% in size and 15% in weight.

Analysis was conducted by holding the articles in a controlled environment for two hours at a temperature of 170° F. The article held at this temperature without melting. The article became slimy when moistened, swelled when hydrated, and became more "wiggly" during hydration.

Articles, cast from the lizard molds, were prepared. From the head to start of the tail was 5.5 inches long and tapered. The head was 1.25 inches, the middle of the body was 1.75 inches, and the tail was 2.50. The article was placed in top and bottom grip attachments of an Instron® Testing Instrument. The top grip was attached at the end of the head where the legs are attached to the trunk of the body. The bottom grip was attached at the end of the trunk of the body where the legs are attached. A 50 kg load transducer was used for the tensile strength test. The load range was set at five to reduce variability in the testing. A strip chart recorder was employed to record the data. A 1:1 recorder to cross head speed was used for the testing. The cross head moved at a speed of 50 mm per minute. The tensile strength of the article was comparable of that of similar shaped plastic articles when tested on the Instron® Universal Testing Instrument using manual grips. A similar shaped plastic article bore a load of 0.98 kg and stretched to 123.6 mm before breaking, while the test article was able to bear a load of 1.08 kg and stretched 119.7 mm before breaking.

Example 7

Digestibility Trials

Formulations (Example 4 and Example 6) were force fed to largemouth bass to determine if the articles would be either broken down or voided from the stomach of a fish. In 2 trials using 6-8 fish per trial, articles placed in the stomachs of fish were completely voided from the stomach within 3-5 days. No adverse reaction by the largemouth bass was noted.

Example 8

Formulation 7

A formulation of the following composition was prepared:

| Component | Amount |
| --- | --- |
| Water | 513 g |
| Glycerol | 100 g |
| Sucrose | 150 g |
| Gelatin (200-300 bloom) | 150 g |
| Kappa carrageenan | 15 g |
| Potassium chloride (KCl) | 3.5 g |
| Potassium sorbate | 3.0 g |
| Fish food powder | 7.5 g |
| Glitter | 5.0 g |
| Food coloring | 15-20 drops |

Manufacturing Procedure: The mixing vessel was charged with water and glycerol. After thorough mixing, the solution was heated to near boiling temperatures. The other ingredients were dry blended. The dry ingredient mixture was added at one time into the hot water/glycerol solution with lots of stirring. The solution was heated in a closed vessel to a temperature of 90-95° C. At this point, the mixture was homogeneous and fluid. The hot solution was injected manually using a syringe into chilled molds (e.g., lizard-shaped, worm-shaped). Gelation occurred almost instantaneously. The strength of the gel was dependent upon holding time and temperature, increasing as time increased and temperature decreased. The articles were hung vertically to cure at 23° C. and 35-40% relative humidity for approximately 3 h. Cured articles were sprayed with vegetable oil and placed into plastic bags. The articles had strength and flexibility. The articles held up under temperatures of 130° C.

Example 9

Formulation 8

A formulation of the following composition was prepared:

| Component | Amount |
| --- | --- |
| Water | 102 g |
| Sucrose | 50 g |
| Gelatin (200-300 bloom) | 30 g |
| Kappa carrageenan | 3 g |
| Locust bean gum | 0.5 g |
| Potassium chloride (KCl) | 0.75 g |

| Component | Amount |
| --- | --- |
| Potassium sorbate | 0.6 g |
| Fish food powder | 1.5 g |
| Glitter | 1.0 g |
| Food coloring | 5-10 drops |

Manufacturing Procedure: The mixing vessel was charged with near-boiling water. The other ingredients were dry blended. The dry ingredient mixture was added at one time into the hot water with lots of stirring. The resultant mixture was much thicker than that of Example 8. The solution was heated in a closed vessel to a temperature of 90-95° C. At this point, the mixture was homogeneous and injectable (it was still thicker than Example 8, making it more difficult to work with). The hot solution was injected manually using a syringe into chilled molds (e.g., lizard-shaped, worm-shaped). Gelation occurred almost instantaneously. The strength of the gel was dependent upon holding time and temperature, increasing as time increased and temperature decreased. The articles were laid flat to cure at 24° C. and 50% relative humidity for approximately 6-8 h. Cured articles were sprayed with vegetable oil and placed into plastic bags. The articles had strength and flexibility. The articles held up under temperatures of 130° C.

Example 10

Formulation 9 with Scale Up

A formulation of the following composition was prepared:

| Component | Amount |
| --- | --- |
| Water | 5 gal |
| Sucrose | 9.2 kg |
| Gelatin (200-300 bloom) | 2.9 kg |
| Kappa carrageenan | 544 g |
| Potassium chloride (KCl) | 114 g |
| Potassium sorbate | 114 g |
| Fish food powder | 151 g |
| Glitter | 151 g |
| Food coloring | 58 mL |

Manufacturing Procedure: Production of fishing lure shaped objects using the above formulation was done at a commercial soft lure manufacturing facility to explore the feasibility of scaling up the process. The mixing vessel was a 15-gallon stainless steel container, which was pressurizable. This vessel also had a valve to allow for injection of sample into the molds. The vessel was equipped with a band heater. Thus, this vessel served to heat, mix, and inject the fluid material. The vessel was charged with water, which was heated to 60-70° C. The other ingredients were dry blended. The dry ingredient mixture was added at one time into the warm water with lots of stirring. The solution was heated in a closed vessel to a minimum temperature of 85° C. (temperature increased during manufacturing. At this point, the mixture was homogeneous and fluid. The hot solution was injected mechanically using pressurized hoses into chilled commercial molds (i.e., lizard-shaped). The injection pressure and hold time were adjusted to yield intact lizards without over-filling the molds (i.e., without flashing). Partial utilization of the batch resulted in the production of 500-600 lizards, which were laid flat on trays to cure. Fresh lizards were fragile and needed to be cured. The curing conditions were 24° C. and 15-20% relative humidity for 8-10 hours. These conditions were actually too harsh, and the lizards were somewhat over-dried. The cured lizards were sprayed with vegetable oil and packaged into plastic bags (10 lizards/bag). The strength of the cured lizards was excellent, but flexibility could be improved. However, the major objective of this project was to evaluate potential problems with commercial production. It was apparent that the formulations can be used with equipment, currently used for plastic articles without significant difficulty.

Example 11

Scale Up with Formulation 6

A formulation in the proportions of Example 6 was also scaled up, resulting in the production of shaped articles again under commercial manufacturing conditions. The higher viscosity of this formulation required higher pressures during injection, which caused some flashing. Different formulations will each require unique optimization of processing conditions. A variety of shapes were prepared successfully. Again, the issues associated with scaling up can be addressed and should not pose significant difficulties.

Example 12

Formulation 10

A formulation of the following composition was prepared:

| Component | Amount |
| --- | --- |
| Water | 63.0 mL |
| Corn Syrup | 35 g |
| Glycerin | 2.3 g |
| Sucrose | 10 g |
| Gelatin (200-300 bloom) | 14.2 g |
| Sodium Alginate | 3.0 g |
| Calcium chloride ($CaCl_2$) | 0.4 g |
| Starch | 2.0 g |
| Sodium Metaphosphate | 1.0 g |
| Locust Bean Gum | 1.0 g |
| Sodium Benzoate | 1.0 g |
| Food coloring | Trace |
| Flavoring | trace |

Manufacturing Procedure: All ingredients are weighed prior, to processing. The water was brought to a boil while the other ingredients were dry blended. The mixing vessel was charged with the hot water. The dry ingredients were added to the hot water with lots of mixing. Food coloring was added. Heating with agitation continued until the temperature reached about 90° C. When all components were completely dissolved in solution and the mixture appeared homogeneous, the hot solution was injected using a syringe into an aluminum mold to yield fish-shaped and lizard-shaped articles. The mold was placed in a refrigerator for about 15 minutes to rapidly obtain a firm gel. The solidified articles were removed from the molds. Curing by storing at ambient temperature varied with humidity and may range from about 10-30 hours, and gave a tougher while still flexible article. The article shrank by about 10% in size and 15% in weight.

Analysis was conducted by holding the articles in a controlled environment for two hours at a temperature of 170° F. The article held at this temperature without melting. The article became slimy when moistened, swelled when hydrated, and became more "wiggly" during hydration.

Articles, cast from the lizard molds, were prepared. From the head to start of the tail was 5.5 inches long and tapered. The head was 1.25 inches, the middle of the body was 1.75 inches, and the tail was 2.50. The lizard was, placed in top and bottom grip attachments of an Instron® Testing Instrument. The top grip was attached at the end of the head where the legs are attached to the trunk of the body. The bottom grip was attached at the end of the trunk of the body where the legs are attached. A 50 kg load transducer was used for the tensile strength test. The load range was set at five to reduce variability in the testing. A strip chart recorder was employed to record the data. A 1:1 recorder to cross head speed was used for the testing. The cross head moved at a speed of 50 mm per minute. The tensile strength of the lizard was comparable of that of a plastic fishing lure when tested on the Instron® Universal Testing Instrument using manual grips. The plastic lure bore a load of 0.98 kg and stretched to 123.6 mm before breaking, while the test lizard was able to bear a load of 1.08 kg and stretched 119.7 mm before breaking. A texture profile analysis was also completed using the Instron® Universal testing instrument. Two factors were identified in the profile: hardness and springness. The plastic lure had a hardness factor of 1.05 and a springness factor of 100%. The test lizard had a hardness factor of 1.25 and a springness factor of 91%.

Example 13

Bait for Oral Rabies Vaccine

A formulation for an oral rabies vaccine for raccoons was prepared:

| Component | Amount (wt %) |
|---|---|
| Water | 44% |
| Corn syrup | 26% |
| Glycerin | 3% |
| Gelatin (200-300 bloom) | 11% |
| Sucrose | 8% |
| Sodium Alginate | 2% |
| Corn Starch | 1% |
| Locust Bean Gum | 1% |
| Sodium Metaphosphate | 1% |
| Calcium chloride | <1% |
| Food coloring | 1% |
| Scent/Flavoring | 2% |
| Food preservative | 1% |

The components of the formulation were admixed.

Once prepared, the formulation was coated on a plastic packet/sachet that contained a placebo for a rabies vaccine by dipping the packet in the formulation material. The coated packet was then allowed to air dry. The plastic packet was approximately 2¼" by ⅞" in size.

Also, in some embodiments of such a bait, a biomarker (e.g., tetracycline hydrochloride) will be included in the formulation or the vaccine.

Alternatively, the packet will be placed on a conveyor of a confectionary enrobing machine that will pour a thin layer of the formulation material over the packet. The coated packet is then sent through a cooling tunnel.

The bait will be distributed to areas known to be inhabited by raccoons. When a raccoon bites the bait, the sachet will get punctured allowing vaccine to enter the animal's mouth and trigger an immune response.

While the Invention has been described with reference to preferred and example embodiments, it will be understood by those skilled in the art that a number of modifications, additions and deletions are within the scope of the invention, as defined by the following claims.

What is claimed is:

1. A method for delivering a vaccine, antibiotic, or contraceptive to a mammal comprising administering to the mammal an oral delivery vehicle comprising:
   a shape formed of a flexible and resilient material, the material comprising:
   about 30 to about 95 wt % on a solids basis of at least one natural or food grade carbohydrate, wherein the carbohydrate comprises sucrose and a starch;
   about 3 to about 50 wt % on a solids basis of at least one natural or food grade protein, wherein the protein comprises gelatin;
   about 1 to about 10 wt % on a solids basis of at least one natural or food grade water-soluble gum, wherein the water-soluble gum comprises locust bean gum;
   sodium alginate, sodium metaphosphate, sodium benzoate, and calcium chloride; and
   a vaccine, antibiotic, or contraceptive.

2. The method of claim 1, wherein the vehicle is a chewable pouch or a capsule.

3. The method of claim 1, wherein the vehicle is a matrix with the medicament suspended therein.

4. The method of claim 1, wherein the vehicle is suitable as an animal food or treat.

5. The method of claim 1, wherein the vaccine, antibiotic, or contraceptive is coated with the material.

6. The method of claim 1, wherein the vehicle is compounded or constructed such that the medicament is time-released from the vehicle.

7. The method of claim 1, wherein the vehicle defines a cavity for containing the medicament.

8. The method of claim 1, wherein the mammal is dog, cat, cattle, horse, raccoon, or deer.

* * * * *